US00PP37334P2

(12) United States Plant Patent
Neu

(10) Patent No.: US PP37,334 P2
(45) Date of Patent: Mar. 17, 2026

(54) ***PELARGONIUM* PLANT NAMED 'KLEPZ24856'**

(50) Latin Name: *Pelargonium zonale*
Varietal Denomination: KLEPZ24856

(71) Applicant: KLEMM + SOHN GMBH & CO. KG, Stuttgart (DE)

(72) Inventor: Nina Neu, Weissach im Tal (DE)

(73) Assignee: Klemm + Sohn GMBH & Co. KG, Stuttgart (DE)

( * ) Notice: Subject to any disclaimer, the term of this patent is extended or adjusted under 35 U.S.C. 154(b) by 0 days.

(21) Appl. No.: 19/188,462

(22) Filed: Apr. 24, 2025

(51) Int. Cl.
*A01H 5/02* (2018.01)
*A01H 6/42* (2018.01)

(52) U.S. Cl.
USPC ..... Plt./329

(58) Field of Classification Search
USPC ..... Plt./263.1, 324, 325, 329
See application file for complete search history.

(56) References Cited

U.S. PATENT DOCUMENTS

PP24,133 P3 12/2013 Klemm et al.
PP29,246 P3 * 4/2018 Klemm ..... A01H 6/42
Plt./360

* cited by examiner

*Primary Examiner* — Karen M Redden
(74) *Attorney, Agent, or Firm* — Weatherly IP Solutions, LLC; Karen P. Bechtold; James M. Weatherly

(57) ABSTRACT

A new *Pelargonium* plant particularly distinguished by no leaf zonation and a purple flower color is disclosed.

1 Drawing Sheet

Genus and species: *Pelargonium zonale*.
Variety denomination: 'KLEPZ24856'.

BACKGROUND OF THE NEW PLANT

The present invention comprises a new and distinct variety of *Pelargonium*, botanically known as *Pelargonium zonale* and hereinafter referred to by the variety name 'KLEPZ24856'. 'KLEPZ24856' originated from a controlled cross in July 2019 in Juja, Kenya between the female *Pelargonium* variety 'PAC Greta' (patent status unknown) and the male *Pelargonium* variety 'KLEPZ11229' (U.S. Plant Pat. No. 24,133).

Seeds from the controlled cross were obtained. The seeds were sown and plants were grown for evaluation. A single plant was selected in June 2020 and subsequently named 'KLEPZ24856'. In July 2020 'KLEPZ24856' was first vegetatively propagated by vegetative stem cuttings in Stuttgart, Germany. 'KLEPZ24856' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. No leaf zonation
2. Purple flower color

DESCRIPTION OF THE PHOTOGRAPH

This new *Pelargonium* plant is illustrated by the accompanying photograph which shows a close-up of the flower of the plant. The photograph is of an approximately 13-week-old plant grown indoors in Stuttgart, Germany. The photograph was taken indoors in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEPZ24856'. Data was collected on 12-week-old plants in Stuttgart, Germany under greenhouse conditions in March 2025. Color references are to The R.H.S. Colour Chart of The Royal Horticultural Society of London (R.H.S.), 5$^{th}$ edition (2007).

Classification:
- *Family*.—Geraniaceae.
- *Botanical*.—*Pelargonium zonale*.
- *Common*.—*Pelargonium*.
- *Designation*.—'KLEPZ24856'.

Parentage:
- *Female parent*.—'PAC Greta' (patent status unknown).
- *Male parent*.—'KLEPZ11229' (U.S. Plant Pat. No. 24,133).

Plant:
- *Form*.—Bushy.
- *Habit*.—Mounding.
- *Height* (*from top of soil*).—14.5 cm.
- *Width* (*horizontal plant diameter*).—23.0 cm.
- *Natural flowering season*.—March to October.
- *Propagation type*.—Vegetative by stem cuttings.
- *Time to produce a finished flowering plant*.—12 weeks.
- *Time to initiate and develop roots*.—4 weeks.
- *Root description*.—Fine, dense, white, RHS 158A.
- *Flower type*.—Zygomorphic.

Stems:
*Quantity of stems per plant.*—3 to 6.
*Color.*—RHS 144A.
*Surface texture.*—Pubescent.
*Stem form.*—Round.
*Diameter.*—0.6 cm.
*Length.*—4.0 cm to 8.0 cm.
*Internode length.*—1.7 cm.
*Anthocyanin.*—None.

Leaves:
*Arrangement.*—Alternate.
*Shape.*—Reniform.
*Apex.*—Round.
*Base.*—Closed.
*Margin.*—Crenate.
*Surface texture both surfaces.*—Both pubescent.
*Length.*—7.8 cm.
*Width.*—8.0 cm.
*Color.*—Upper surface: RHS 137A. Lower surface: RHS 137C.
*Zonation.*—No.
*Depth of Sinus.*—2.5 cm.
*Petiole.*—Length: 4.0 cm to 5.0 cm. Diameter: 0.3 cm. Color: RHS 144A. Strength: Medium.
*Venation pattern.*—Palmate.
*Venation color.*—Upper surface: RHS 137A. Lower surface: RHS 144A.

Inflorescence:
*Lastingness of flowers on the plant.*—6 to 8 days.
*Umbels.*—Quantity of umbels per plant: 3 to 6. Length: 4.5 cm. Diameter: 7.0 cm.
*Individual florets of the umbel.*—Quantity of florets per umbel: 10. Depth: 1.4 cm. Diameter: 4.5 cm.
*Fragrance.*—Absent.

Flower buds:
*Cluster shape.*—Round.
*Cluster size.*—Length: 1.0 cm. Width: 1.6 cm.
*Surface texture.*—Pubescent.
*Bud.*—Height: 0.6 cm. Width: 0.5 cm. Shape: Round. Apex: Acute. Base: Obtuse. Margin: Entire. Color: RHS 144A.

Petals:
*Quantity per flower.*—5.
*Shape.*—Spatulate.
*Apex.*—Round.
*Base.*—Obtuse.
*Margin.*—Entire.
*Length.*—2.5 cm.
*Width.*—2.5 cm.
*Surface texture.*—Upper surface: Smooth. Lower surface: Smooth.
*Color of lobes.*—Upper lobes: Upper surface: RHS N78B basic color, RHS 84D markings at base of petals. Lower surface: RHS 84B. Lower lobes: Upper surface: RHS N78B basic color. Lower surface: RHS 84B.

Petaloids:
*Quantity per flower.*—0 to 2.
*Shape.*—Crippled and deformed spatulate.
*Apex.*—Obtuse or round.
*Base.*—Obtuse.
*Margin.*—Entire.
*Length.*—0.5 cm to 1.5 cm.
*Width.*—0.5 cm to 1.0 cm.
*Surface texture.*—Upper surface: Smooth. Lower surface: Smooth.
*Color.*—Upper surface: RHS N78B. Lower surface: RHS 84B.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Pubescent.
*Color.*—Upper surface: RHS 144A. Lower surface: RHS 144A.
*Length.*—1.1 cm.
*Width.*—0.2 cm.

Pedicel:
*Length.*—2.6 cm.
*Diameter.*—0.2 cm.
*Color.*—RHS 152A.
*Surface texture.*—Pubescent.
*Strength.*—Medium.

Peduncle:
*Length.*—9.0 cm.
*Diameter.*—0.3 cm.
*Color.*—RHS 144A.
*Texture.*—Pubescent.
*Strength.*—Medium.

Reproductive organs:
*Stamens.*—Quantity per flower: 5 to 7. Anther length: 0.1 cm. Filament length: 0.8 cm. Filament color: RHS NN155D. Pollen amount: Medium. Pollen color: RHS N167A.
*Pistils.*—Number: 1. Stigma color: RHS 67A. Style length: 0.2 cm. Style color: RHS 67A. Ovary arrangement: Central. Ovary color: RHS 175A. Ovary diameter: 0.2 cm. Ovary length: 0.5 cm. Ovary Texture: Pubescent.

Fruit and seed set: None observed.
Disease and pest/insect resistance: None observed.

COMPARISON WITH PARENTAL LINES AND KNOWN VARIETY

'KLEPZ24856' is distinguished from its parents as described in Table 1.

TABLE 1

Comparison with Parental Lines

| Characteristic | 'KLEPZ24856' | Female parent | Male parent |
|---|---|---|---|
| Flower basic color | Purple | Lavender | Lavender pink |

'KLEPZ24856' can be compared to the commercial variety 'PAC Violetta' (patent status unknown). Differences between the two varieties are described in Table 2:

TABLE 2

Comparison with Similar Variety

| Characteristic | 'KLEPZ24856' | 'PAC Violetta' |
|---|---|---|
| Leaf zonation | None | Weak |
| Crippled petaloids | 0 to 2 | 3 to 4 |
| Flower color | Purple | Pink purple |

I claim:

1. A new and distinct variety of *Pelargonium* plant named 'KLEPZ24856' as illustrated and described herein.

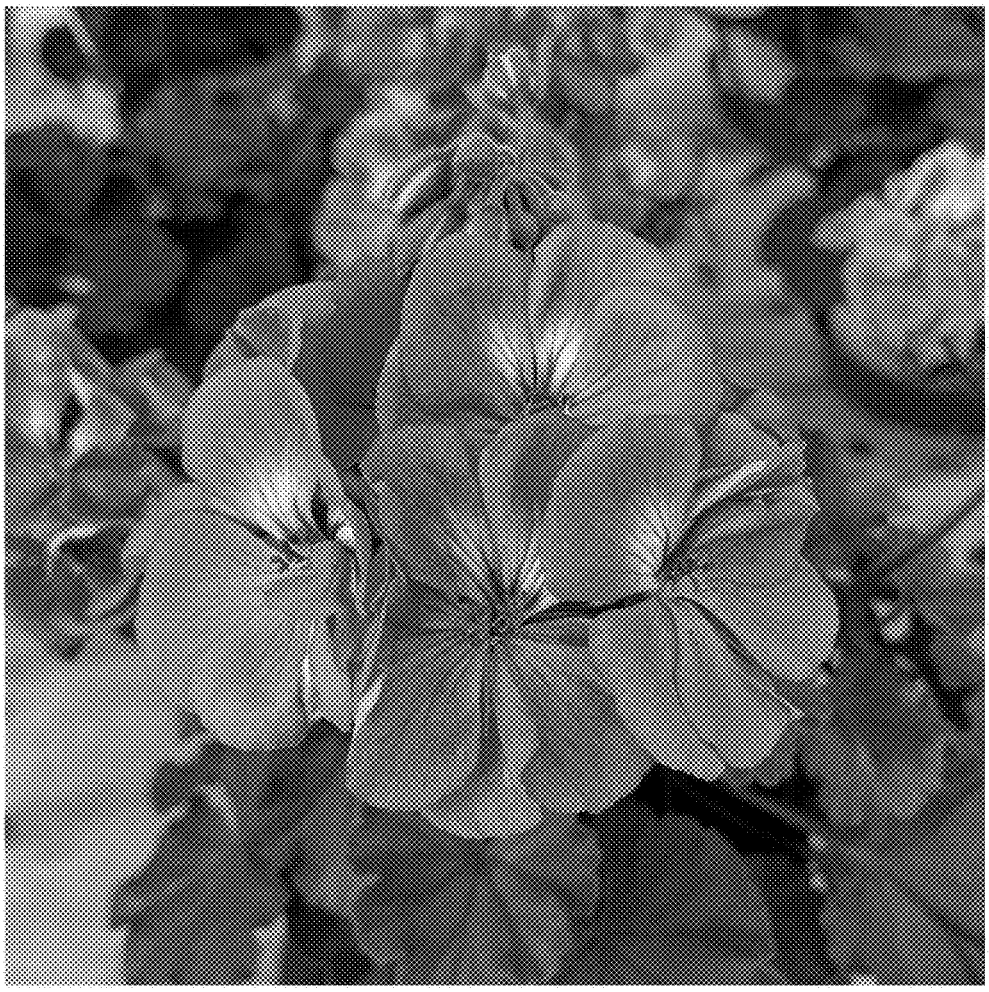

* * * * *